(12) United States Patent
Braido

(10) Patent No.: US 12,156,809 B2
(45) Date of Patent: Dec. 3, 2024

(54) STENT DESIGNS FOR PROSTHETIC HEART VALVES

(71) Applicant: St. Jude Medical, Cardiology Division, Inc., St. Paul, MN (US)

(72) Inventor: Peter N. Braido, Wyoming, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 593 days.

(21) Appl. No.: 17/211,950

(22) Filed: Mar. 25, 2021

(65) Prior Publication Data
US 2021/0205081 A1 Jul. 8, 2021

Related U.S. Application Data

(60) Division of application No. 16/172,099, filed on Oct. 26, 2018, now Pat. No. 10,993,804, which is a (Continued)

(51) Int. Cl.
*A61F 2/24* (2006.01)

(52) U.S. Cl.
CPC .......... *A61F 2/2418* (2013.01); *A61F 2/2412* (2013.01); *A61F 2210/0061* (2013.01); (Continued)

(58) Field of Classification Search
None
See application file for complete search history.

(56) References Cited

U.S. PATENT DOCUMENTS 3,657,744 A 4/1972 Ersek
4,275,469 A 6/1981 Gabbay
(Continued)

FOREIGN PATENT DOCUMENTS

DE 19857887 A1 7/2000
DE 10121210 B4 11/2005
(Continued)

OTHER PUBLICATIONS

E. Grube et al., "Percutaneous Implantation of the CoreValve Self-Expanding Valve Prothesis in High-Risk Patients With Aortic Valve Disease. The Siegburg First-in-Man Study", Circulation, (20060000), vol. 114, pp. 1616-1624, XP055342562.
(Continued)

*Primary Examiner* — Leslie A Lopez
(74) *Attorney, Agent, or Firm* — SLEMAN & LUND LLP

(57) ABSTRACT

A prosthetic heart valve includes a collapsible and expandable stent, a cuff attached to an annulus section of the stent, and leaflets attached to the cuff between a first location and a second location distal to the first location in a flow direction. The stent may include struts shaped to form a plurality of cells connected to one another in annular rows around the stent. The cuff may have top and bottom edges and may occupy a first group of the cells, such that cells above the top edge are open cells at least partially devoid of the cuff. The cuff may have a landing zone extending at least one-third of a length of the stent in the flow direction between the bottom edge of the cuff and a proximal end of a most proximal cell of the open cells when the stent is in an expanded use condition.

19 Claims, 5 Drawing Sheets

Related U.S. Application Data continuation of application No. 14/479,947, filed on Sep. 8, 2014, now Pat. No. 10,117,742.

(60) Provisional application No. 61/876,989, filed on Sep. 12, 2013.

(52) U.S. Cl.
CPC .............. *A61F 2220/0075* (2013.01); *A61F 2230/0054* (2013.01); *A61F 2230/008* (2013.01); *A61F 2250/0069* (2013.01)

(56) References Cited

U.S. PATENT DOCUMENTS

| | | |
|---|---|---|
| 4,423,730 A | 1/1984 | Gabbay |
| 4,491,986 A | 1/1985 | Gabbay |
| 4,759,758 A | 7/1988 | Gabbay |
| 4,816,029 A | 3/1989 | Penny, III et al. |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,415,664 A | 5/1995 | Pinchuk |
| 5,480,423 A | 1/1996 | Ravenscroft et al. |
| 5,843,167 A | 12/1998 | Dwyer et al. |
| 5,855,601 A | 1/1999 | Bessler et al. |
| 5,924,424 A | 7/1999 | Stevens et al. |
| 5,935,163 A | 8/1999 | Gabbay |
| 5,961,549 A | 10/1999 | Nguyen et al. |
| 5,968,068 A | 10/1999 | Dehdashtian et al. |
| 6,045,576 A | 4/2000 | Starr et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,306,141 B1 | 10/2001 | Jervis |
| 6,368,348 B1 | 4/2002 | Gabbay |
| 6,419,695 B1 | 7/2002 | Gabbay |
| 6,458,153 B1 | 10/2002 | Bailey et al. |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,652,578 B2 | 11/2003 | Bailey et al. |
| 6,685,625 B2 | 2/2004 | Gabbay |
| 6,716,244 B2 | 4/2004 | Klaco |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 6,951,573 B1 | 10/2005 | Dilling |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,195,641 B2 | 3/2007 | Palmaz et al. |
| 7,247,167 B2 | 7/2007 | Gabbay |
| 7,267,686 B2 | 9/2007 | DiMatteo et al. |
| 7,276,078 B2 | 10/2007 | Spenser et al. |
| 7,311,730 B2 | 12/2007 | Gabbay |
| 7,320,704 B2 | 1/2008 | Lashinski et al. |
| 7,329,278 B2 | 2/2008 | Seguin et al. |
| 7,374,573 B2 | 5/2008 | Gabbay |
| 7,381,218 B2 | 6/2008 | Schreck |
| 7,381,219 B2 | 6/2008 | Salahieh et al. |
| 7,452,371 B2 | 11/2008 | Pavonik et al. |
| 7,510,572 B2 | 3/2009 | Gabbay |
| 7,510,575 B2 | 3/2009 | Spenser et al. |
| 7,524,331 B2 | 4/2009 | Birdsall |
| 7,534,261 B2 | 5/2009 | Friedman |
| RE40,816 E | 6/2009 | Taylor et al. |
| 7,585,321 B2 | 9/2009 | Cribier |
| 7,628,805 B2 | 12/2009 | Spenser et al. |
| 7,682,390 B2 | 3/2010 | Seguin |
| 7,708,775 B2 | 5/2010 | Rowe et al. |
| 7,731,742 B2 | 6/2010 | Schlick et al. |
| 7,748,389 B2 | 7/2010 | Salahieh et al. |
| 7,780,725 B2 | 8/2010 | Haug et al. |
| 7,799,069 B2 | 9/2010 | Bailey et al. |
| 7,803,185 B2 | 9/2010 | Gabbay |
| 7,824,442 B2 | 11/2010 | Salahieh et al. |
| 7,837,727 B2 | 11/2010 | Goetz et al. |
| 7,846,203 B2 | 12/2010 | Cribier |
| 7,846,204 B2 | 12/2010 | Letac et al. |
| 7,857,845 B2 | 12/2010 | Stacchino et al. |
| 7,892,281 B2 | 2/2011 | Seguin et al. |
| 7,914,569 B2 | 3/2011 | Nguyen et al. |
| 7,959,666 B2 | 6/2011 | Salahieh et al. |
| 7,959,672 B2 | 6/2011 | Salahieh et al. |
| 7,972,378 B2 | 7/2011 | Tabor et al. |
| 7,988,724 B2 | 8/2011 | Salahieh et al. |
| 7,993,394 B2 | 8/2011 | Hariton et al. |
| 8,016,877 B2 | 9/2011 | Seguin et al. |
| D648,854 S | 11/2011 | Braido |
| 8,048,153 B2 | 11/2011 | Salahieh et al. |
| 8,052,741 B2 | 11/2011 | Bruszewski et al. |
| 8,052,749 B2 | 11/2011 | Salahieh et al. |
| 8,052,750 B2 | 11/2011 | Tuval et al. |
| 8,062,355 B2 | 11/2011 | Figulla et al. |
| 8,075,611 B2 | 12/2011 | Millwee et al. |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| 8,137,398 B2 | 3/2012 | Tuval et al. |
| 8,142,497 B2 | 3/2012 | Friedman |
| D660,432 S | 5/2012 | Braido |
| D660,433 S | 5/2012 | Braido et al. |
| D660,967 S | 5/2012 | Braido et al. |
| 8,182,528 B2 | 5/2012 | Salahieh et al. |
| 8,221,493 B2 | 7/2012 | Boyle et al. |
| 8,230,717 B2 | 7/2012 | Matonick |
| 8,231,670 B2 | 7/2012 | Salahieh et al. |
| 8,252,051 B2 | 8/2012 | Chau et al. |
| 8,308,798 B2 | 11/2012 | Pintor et al. |
| 8,313,525 B2 | 11/2012 | Tuval et al. |
| 8,323,335 B2 | 12/2012 | Rowe et al. |
| 8,323,336 B2 | 12/2012 | Hill et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,348,998 B2 | 1/2013 | Pintor et al. |
| 8,366,769 B2 | 2/2013 | Huynh et al. |
| 8,403,983 B2 | 3/2013 | Quadri et al. |
| 8,408,214 B2 | 4/2013 | Spenser |
| 8,414,643 B2 | 4/2013 | Tuval et al. |
| 8,425,593 B2 | 4/2013 | Braido et al. |
| 8,449,599 B2 | 5/2013 | Chau et al. |
| 8,449,604 B2 | 5/2013 | Moaddeb et al. |
| D684,692 S | 6/2013 | Braido |
| 8,454,686 B2 | 6/2013 | Alkhatib |
| 8,500,798 B2 | 8/2013 | Rowe et al. |
| 8,568,474 B2 | 10/2013 | Yeung et al. |
| 8,579,962 B2 | 11/2013 | Salahieh et al. |
| 8,579,966 B2 | 11/2013 | Seguin et al. |
| 8,585,755 B2 | 11/2013 | Chau et al. |
| 8,591,575 B2 | 11/2013 | Cribier |
| 8,597,349 B2 | 12/2013 | Alkhatib |
| 8,603,159 B2 | 12/2013 | Seguin et al. |
| 8,603,160 B2 | 12/2013 | Salahieh et al. |

(56) References Cited

U.S. PATENT DOCUMENTS

| | | |
|---|---|---|
| 8,613,765 B2 | 12/2013 | Bonhoeffer et al. |
| 8,623,074 B2 | 1/2014 | Ryan |
| 8,652,204 B2 | 2/2014 | Quill et al. |
| 8,663,322 B2 | 3/2014 | Keranen |
| 8,668,733 B2 | 3/2014 | Haug et al. |
| 8,685,080 B2 | 4/2014 | White |
| 8,728,154 B2 | 5/2014 | Alkhatib |
| 8,747,459 B2 | 6/2014 | Nguyen et al. |
| 8,764,820 B2 | 7/2014 | Dehdashtian et al. |
| 8,795,357 B2 | 8/2014 | Yohanan et al. |
| 8,801,776 B2 | 8/2014 | House et al. |
| 8,808,356 B2 | 8/2014 | Braido et al. |
| 8,828,078 B2 | 9/2014 | Salahieh et al. |
| 8,834,563 B2 | 9/2014 | Righini |
| 8,840,661 B2 | 9/2014 | Manasse |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,940,040 B2 | 1/2015 | Shahriari |
| 8,945,209 B2 | 2/2015 | Bonyuet et al. |
| 8,961,595 B2 | 2/2015 | Alkhatib |
| 8,974,523 B2 | 3/2015 | Thill et al. |
| 8,974,524 B2 | 3/2015 | Yeung et al. |
| 9,326,856 B2 | 5/2016 | Schraut et al. |
| 9,820,852 B2 | 11/2017 | Braido et al. |
| 9,889,004 B2 | 2/2018 | Braido |
| 2002/0036220 A1 | 3/2002 | Gabbay |
| 2003/0014104 A1 | 1/2003 | Cribier |
| 2003/0023303 A1 | 1/2003 | Palmaz et al. |
| 2003/0040792 A1 | 2/2003 | Gabbay |
| 2003/0050694 A1 | 3/2003 | Yang et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0111111 A1 | 6/2004 | Lin |
| 2004/0186563 A1 | 9/2004 | Lobbi |
| 2004/0210304 A1 | 10/2004 | Seguin et al. |
| 2004/0260389 A1 | 12/2004 | Case et al. |
| 2005/0075720 A1 | 4/2005 | Nguyen et al. |
| 2005/0096726 A1 | 5/2005 | Sequin et al. |
| 2005/0137682 A1 | 6/2005 | Justino |
| 2005/0137687 A1 | 6/2005 | Salahieh et al. |
| 2005/0137695 A1 | 6/2005 | Salahieh et al. |
| 2005/0137697 A1 | 6/2005 | Salahieh et al. |
| 2005/0137701 A1 | 6/2005 | Salahieh et al. |
| 2005/0203605 A1 | 9/2005 | Dolan |
| 2005/0240200 A1 | 10/2005 | Bergheim |
| 2005/0256566 A1 | 11/2005 | Gabbay |
| 2006/0008497 A1 | 1/2006 | Gabbay |
| 2006/0074484 A1 | 4/2006 | Huber |
| 2006/0106415 A1 | 5/2006 | Gabbay |
| 2006/0122692 A1 | 6/2006 | Gilad et al. |
| 2006/0142848 A1 | 6/2006 | Gabbay |
| 2006/0149360 A1 | 7/2006 | Schwammenthal et al. |
| 2006/0161249 A1 | 7/2006 | Realyvasquez et al. |
| 2006/0167468 A1 | 7/2006 | Gabbay |
| 2006/0173532 A1 | 8/2006 | Flagle et al. |
| 2006/0178740 A1 | 8/2006 | Stacchino et al. |
| 2006/0195180 A1 | 8/2006 | Kheradvar et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259136 A1* | 11/2006 | Nguyen ............... A61F 2/2415 623/2.18 |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2006/0276874 A1 | 12/2006 | Wilson et al. |
| 2006/0287717 A1 | 12/2006 | Rowe et al. |
| 2007/0010876 A1 | 1/2007 | Salahieh et al. |
| 2007/0016285 A1 | 1/2007 | Lane et al. |
| 2007/0027534 A1 | 2/2007 | Bergheim et al. |
| 2007/0043431 A1 | 2/2007 | Melsheimer |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0073387 A1 | 3/2007 | Forster et al. |
| 2007/0073391 A1 | 3/2007 | Bourang et al. |
| 2007/0088431 A1 | 4/2007 | Bourang et al. |
| 2007/0093890 A1 | 4/2007 | Eliasen et al. |
| 2007/0100435 A1 | 5/2007 | Case et al. |
| 2007/0112422 A1 | 5/2007 | Dehdashtian |
| 2007/0118210 A1 | 5/2007 | Pinchuk |
| 2007/0162100 A1 | 7/2007 | Gabbay |
| 2007/0168013 A1 | 7/2007 | Douglas |
| 2007/0203575 A1 | 8/2007 | Forster et al. |
| 2007/0213813 A1 | 9/2007 | Von Segesser et al. |
| 2007/0233228 A1 | 10/2007 | Eberhardt et al. |
| 2007/0239271 A1 | 10/2007 | Nguyen |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147182 A1 | 6/2008 | Righini et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0054975 A1 | 2/2009 | del Nido et al. |
| 2009/0099653 A1 | 4/2009 | Suri et al. |
| 2009/0112309 A1 | 4/2009 | Jaramillo et al. |
| 2009/0138079 A1 | 5/2009 | Tuval et al. |
| 2009/0276027 A1 | 11/2009 | Glynn |
| 2009/0276040 A1 | 11/2009 | Rowe et al. |
| 2009/0287299 A1 | 11/2009 | Tabor et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0082094 A1 | 4/2010 | Quadri et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0168844 A1 | 7/2010 | Toomes et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0234940 A1 | 9/2010 | Dolan |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1* | 11/2010 | Quadri ............... A61F 2/95 623/2.11 |
| 2011/0029072 A1 | 2/2011 | Gabbay |
| 2011/0054466 A1 | 3/2011 | Rothstein et al. |
| 2011/0098800 A1 | 4/2011 | Braido et al. |
| 2011/0098802 A1* | 4/2011 | Braido ............... A61F 2/2409 623/2.11 |
| 2011/0137397 A1 | 6/2011 | Chau et al. |
| 2011/0172765 A1 | 7/2011 | Nguyen et al. |
| 2011/0208283 A1 | 8/2011 | Rust |
| 2011/0224678 A1 | 9/2011 | Gabbay |
| 2011/0238168 A1 | 9/2011 | Pellegrini et al. |
| 2011/0251675 A1* | 10/2011 | Dwork ............... A61F 2/2418 623/1.26 |
| 2011/0264206 A1 | 10/2011 | Tabor |
| 2011/0295363 A1* | 12/2011 | Girard ............... A61F 2/2412 623/1.26 |
| 2012/0035722 A1 | 2/2012 | Tuval |
| 2012/0041550 A1 | 2/2012 | Salahieh et al. |
| 2012/0053681 A1 | 3/2012 | Alkhatib et al. |

(56) References Cited

U.S. PATENT DOCUMENTS

| | | |
|---|---|---|
| 2012/0071969 A1 | 3/2012 | Li et al. |
| 2012/0078347 A1 | 3/2012 | Braido et al. |
| 2012/0078350 A1 | 3/2012 | Wang et al. |
| 2012/0101572 A1 | 4/2012 | Kovalsky et al. |
| 2012/0123529 A1 | 5/2012 | Levi et al. |
| 2012/0143324 A1 | 6/2012 | Rankin et al. |
| 2012/0303116 A1 | 11/2012 | Gorman, III et al. |
| 2012/0316642 A1 | 12/2012 | Yu |
| 2013/0018458 A1 | 1/2013 | Yohanan et al. |
| 2013/0274873 A1 | 10/2013 | Delaloye et al. |
| 2013/0304200 A1 | 11/2013 | McLean et al. |
| 2013/0331929 A1 | 12/2013 | Mitra et al. |
| 2014/0005771 A1 | 1/2014 | Braido et al. |
| 2014/0121763 A1 | 5/2014 | Duffy et al. |
| 2014/0155997 A1 | 6/2014 | Braido |
| 2014/0214159 A1 | 7/2014 | Vidlund et al. |
| 2014/0228946 A1 | 8/2014 | Chau et al. |
| 2014/0303719 A1 | 10/2014 | Cox et al. |
| 2014/0324164 A1 | 10/2014 | Gross et al. |
| 2014/0343671 A1 | 11/2014 | Yohanan et al. |
| 2014/0350668 A1 | 11/2014 | Delaloye et al. |
| 2014/0350669 A1 | 11/2014 | Gillespie et al. |

FOREIGN PATENT DOCUMENTS

| | | | |
|---|---|---|---|
| DE | 102005003632 A1 | 8/2006 | |
| DE | 202008009610 U1 | 12/2008 | |
| EP | 0850607 A1 | 7/1998 | |
| EP | 1000590 A1 | 5/2000 | |
| EP | 1584306 A1 | 10/2005 | |
| EP | 1598031 A2 | 11/2005 | |
| EP | 1360942 B1 | 12/2005 | |
| EP | 1926455 A2 | 6/2008 | |
| EP | 2537487 A1 | 12/2012 | |
| EP | 2870946 A1 | 5/2015 | |
| EP | 2898859 A1 | 7/2015 | |
| EP | 2898859 B1 | 11/2018 | |
| FR | 2850008 A1 | 7/2004 | |
| FR | 2847800 B1 | 10/2005 | |
| NO | 9117720 A1 | 11/1991 | |
| WO | 9716133 A1 | 5/1997 | |
| WO | 9832412 A2 | 7/1998 | |
| WO | 9913801 A1 | 3/1999 | |
| WO | 200128459 A1 | 4/2001 | |
| WO | 200149213 A2 | 7/2001 | |
| WO | 200156500 A2 | 8/2001 | |
| WO | 2001054625 A1 | 8/2001 | |
| WO | 2001076510 A2 | 10/2001 | |
| WO | 200236048 A1 | 5/2002 | |
| WO | 0247575 A2 | 6/2002 | |
| WO | 02067782 A2 | 9/2002 | |
| WO | 2003047468 A1 | 6/2003 | |
| WO | 2005062980 A2 | 7/2005 | |
| WO | 2005070343 A1 | 8/2005 | |
| WO | 06073626 A2 | 7/2006 | |
| WO | 2007071436 A2 | 6/2007 | |
| WO | WO-2007081820 A1 * | 7/2007 | ........... A61F 2/2418 |
| WO | 2008070797 A2 | 6/2008 | |
| WO | 2009024859 A2 | 2/2009 | |
| WO | 2009042196 A2 | 4/2009 | |
| WO | 2010008548 A2 | 1/2010 | |
| WO | 2010008549 A1 | 1/2010 | |
| WO | 2010096176 A1 | 8/2010 | |
| WO | 2010098857 A1 | 9/2010 | |
| WO | 2011133787 A1 | 10/2011 | |
| WO | 2012048035 A2 | 4/2012 | |
| WO | 2012177942 A2 | 12/2012 | |
| WO | 2013012801 | 1/2013 | |
| WO | 2013028387 A2 | 2/2013 | |
| WO | 2013086413 | 6/2013 | |
| WO | 2014066017 | 5/2014 | |
| WO | 2014110210 | 7/2014 | |
| WO | 2014127750 | 8/2014 | |
| WO | 2014163704 A1 | 10/2014 | |
| WO | 2014164149 | 10/2014 | |
| WO | 2014164151 A1 | 10/2014 | |
| WO | 2014179782 | 11/2014 | |
| WO | 2014204807 | 12/2014 | |
| WO | 2015077274 A1 | 5/2015 | |

OTHER PUBLICATIONS

Grube et al., "Percutaneous Aortic Valve Replacement for Severe Aortic Stenosis in High-Risk Patients Using the Second- and Current Third- Generation Self-Expanding CoreValve Prosthesis", JACC, (Jul. 3, 2007), vol. 50, No. 1, doi:10.1016/j.jacc.2007.04. 047, pp. 69-76, XP029653338.

"Closed heart surgery: Back to the future", Samuel V. Lichtenstein, The Journal of Thoracic and Cardiovascular Surgery, vol. 131, No. 5, pp. 941-943.

"Direct-Access Valve Replacement", Christoph H. Huber, et al., Journal of the American College of Cardiology, vol. 46, No. 2, (Jul. 19, 2005).

"Minimally invasive cardiac surgery", M. J. Mack, Surgical Endoscopy, 2006, 20:S488-S492, DOI: 10.1007/s00464-006-0110-8 (presented Apr. 24, 2006).

"Percutaneous Aortic Valve Implantation Retrograde From the Femoral Artery", John G. Webb et al., Circulation, 2006; 113:842-850 (Feb. 6, 2006).

"Transapical aortic valve implantation: an animal feasibility study"; Todd M. Dewey et al., The annals of thoracic surgery 2006; 82: 110-6 (Feb. 13, 2006).

"Transapical approach for sutureless stent-fixed aortic valve implantation: experimental results"; Th. Walther et al., European Journal of Cardio-thoracic Surgery 29 (2006) 703-708 (Jan. 30, 2006).

"Transapical Transcatheter Aortic Valve Implantation in Humans", Samuel V. Lichtenstein et al., Circulation. 2006; 114: 591-596 (Jul. 31, 2006).

Braido et al., Design U.S. Appl. No. 29/375,243, filed Sep. 20, 2010.

Braido, Peter N., U.S. Appl. No. 61/931,265, filed Jan. 24, 2014; Stationary Intra-Annular Halo Designs for Paravalvular Leak (PVL) Reduction—Active Channel Filling Cuff Designs.

Braido, Peter Nicholas, U.S. Appl. No. 29/375,260, filed Sep. 20, 2010, titled "Forked Ends".

Buellesfeld et al., Treatment of paravalvular leaks through inverventional techniques; Department of Cardiology, Ben University Hospital 2011.

Catheter-implanted prosthetic heart valves, Knudsen, L.L., et al., The International Journal of Artificial Organs, vol. 16, No. 5 1993, pp. 253-262.

De Cicco, Giuseppe, et al. "Aortic valve periprosthetic leakage: anatomic observations and surgical results." The Annals of thoracic surgery 79.5 (2005): 1480-1485.

Extended European Search Report for Application No. 15152315.6 dated May 29, 2015.

Extended European Search Report for Application No. 15152324.8 dated Jun. 10, 2015.

Gössl, Mario, and Charanjit S. Rihal. "Percutaneous treatment of aortic and mitral valve paravalvular regurgitation." Current cardiology reports 15.8 (2013): 1-8.

Heat Advisor, "Heart repairs without surgery. Minimally invasive procedures aim to correct valve leakage", Sep. 2004, PubMed ID 15586429.

International Search Report & Written Opinion for Application No. PCT/US2014/054485 dated Nov. 20, 2014.

International Search Report and Written Opinion for Application No. PCT/US2015/011387 dated Mar. 30, 2015.

Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.

Muñoz, et al., "Guidance of treatment of perivalvular prosthetic leaks.", Current cardiology reports, 16.430, 6 pages, Jan. 2014.

Percutaneous aortic valve replacement: resection before implantation, 836-840, Quaden, Rene et al., European J. of Cardio-thoracic Surgery, 27 (2005).

(56) References Cited

OTHER PUBLICATIONS

Preliminary Opinion of the Opposition Division Indicating Issue of Summons to Follow at a Later Time and Shorter Notice for EP15152324.8 dated May 13, 2020; 12 pages.
Rohde, et al., "Resection of Calcified Aortic Heart Leaflets In Vitro by Q-Switched 2 µm Microsecond Laser Radiation", Journal of Cardiac Surgery, 30(2):157-62. Feb. 2015.
Ruiz, Carlos, Overview of PRE-CE Mark Transcatheter Aortic Valve Technologies, Euro PCR, dated May 25, 2010.
Swiatkiewicz, Iwona, et al. "Percutaneous closure of mitral perivalvular leak." Kardiologia polska 67.7 (2009): 762.
Textbook "Transcatheter Valve Repair", 2006, pp. 165-186.
Transcatheter Umbrella Closure of Valvular and Paravalvular Leaks, Hourihan et al., Journal of the American College of Cardiology, vol. 20, No. 6, pp. 1371-1377, (1992).
Transluminal Aortic Valve Placement, Moazami, Nader, et al., ASAIO Journal, 1996; 42:M381-M385.
Transluminal Catheter Implanted Prosthetic Heart Valves, Andersen, Henning Rud, International Journal of Angiology 7:102-106 (1998).
Transluminal implantation of artificial heart valves, Andersen, H. R., et al., European Heart Journal (1992) 13, 704-708.
International Search Report for Application No. PCT/US2015/011387 dated Mar. 30, 2015.
International Search Report for Application No. PCT/US2014/054485 dated Nov. 20, 2014.

\* cited by examiner

STENT DESIGNS FOR PROSTHETIC HEART VALVES

CROSS-REFERENCE TO RELATED APPLICATIONS

This application is a divisional of U.S. application Ser. No. 16/172,099 filed Oct. 26, 2018, which is a continuation of U.S. application Ser. No. 14/479,947, filed on Sep. 8, 2014, now U.S. Pat. No. 10,117,742, which claims the benefit of the filing date of U.S. Provisional Patent Application No. 61/876,989 filed on Sep. 12, 2013, the disclosures of which are hereby incorporated herein by reference.

BACKGROUND OF THE INVENTION

The present invention relates to heart valve replacement and, in particular, to collapsible prosthetic heart valves. More particularly, the present invention relates to collapsible prosthetic heart valves having improved stent designs.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the valve, assuring its proper location, and then expanding a balloon positioned within the valve stent. For self-expanding valves, on the other hand, the stent automatically expands as the sheath covering the valve is withdrawn.

BRIEF SUMMARY OF THE INVENTION

Prosthetic heart valves and methods of expanding a prosthetic heart valve between native leaflets of a native aortic annulus of a patient are disclosed.

A prosthetic heart valve configured to be expanded between native leaflets of a native aortic annulus of a patient may include a collapsible and expandable stent, a cuff attached to the stent, and a plurality of prosthetic valve leaflets attached to the cuff. The stent may have a proximal end, a distal end, an annulus section adjacent the proximal end, and an aortic section adjacent the distal end. The stent may include a plurality of struts shaped to form a plurality of cells connected to one another in a plurality of annular rows around the stent. The stent may define a flow direction from the proximal end toward the distal end. The stent may have a minimum diameter in a direction perpendicular to the flow direction and a length in the flow direction between the proximal and distal ends when the stent is in an expanded use condition, the length being greater than the minimum diameter.

The cuff may be attached to the annulus section of the stent. The cuff may have top and bottom edges and may occupy a first group of the cells, such that the cells above the top edge are open cells at least partially devoid of the cuff. The cuff may have a landing zone extending at least one-third of the length of the stent in the flow direction between the bottom edge of the cuff and a proximal end of a most proximal cell of the open cells when the stent is in the expanded use condition. The prosthetic valve leaflets may be attached to the cuff between a first location and a second location distal to the first location in the flow direction, each of the prosthetic valve leaflets having a free edge.

A prosthetic heart valve configured to be expanded between native leaflets of a native aortic annulus of a patient may include a collapsible and expandable stent, a cuff attached to the stent, and a plurality of prosthetic valve leaflets attached to the cuff. The stent may have a proximal end, a distal end, an annulus section adjacent the proximal end, and an aortic section adjacent the distal end. The stent may include a plurality of struts shaped to form a plurality of cells connected to one another in a plurality of annular rows around the stent. The stent may define a flow direction from the proximal end toward the distal end.

The cuff may be attached to the annulus section of the stent. The cuff may have top and bottom edges and occupying a first group of the cells, such that the cells above the top edge are open cells at least partially devoid of the cuff. The cuff may have a landing zone extending at least 16 mm in the flow direction between the bottom edge of the cuff and a proximal end of a most proximal cell of the open cells when the stent is in an expanded use condition. The plurality of prosthetic valve leaflets may be attached to the cuff between a first location and a second location distal to the first location in the flow direction. Each of the prosthetic valve leaflets may have a free edge.

The landing zone may extend at least 16 mm in the flow direction between the bottom edge of the cuff and the proximal end of the most proximal cell of the open cells when the stent is in an expanded use condition. The entire free edge of each of the prosthetic valve leaflets may be located within a first distance in the flow direction from the distal end of the stent when the prosthetic valve leaflets are in the open position and the stent is in the expanded use condition, the first distance being less than a length of the landing zone in the flow direction.

The cuff may include a proximal portion and a distal portion. The proximal portion may be coupled to a first group of the plurality of struts adjacent the bottom edge and may have a first average thickness in a radial direction perpendicular to the flow direction. The distal portion may be coupled to a second group of the plurality of struts adjacent the top edge and may have a second average thickness in the radial direction, the first average thickness being greater than the second average thickness. Substantially all of the proximal portion of the cuff may be located between the first location and the proximal end of the stent. The cuff may be disposed on a luminal surface of the stent.

The distal portion of the cuff may include a plurality of pockets containing a material that is configured to swell in size when contacted by blood. The proximal portion of the cuff may occupy every cell in a first row of the annular rows of cells. The distal portion of the cuff may occupy every cell in a second row of the annular rows of cells adjacent the first row. The distal portion of the cuff may also occupy a subset of cells in a third row of the annular rows of cells adjacent the second row such that at least some of the open cells are located in the third row.

The proximal portion of the cuff may be initially separate from the distal portion of the cuff and may be coupled to a bottom edge of the distal portion of the cuff at a top edge of the proximal portion of the cuff. The proximal portion of the cuff and the distal portion of the cuff may be made of different materials. The proximal portion of the cuff and the distal portion of the cuff may be joined to one another along a boundary line that extends between adjacent rows of the annular rows of cells. The proximal portion of the cuff and the distal portion of the cuff may be joined to one another along a boundary line that extends in a substantially circular closed curve about a circumference of the stent, the curve lying in a plane generally perpendicular to the flow direction.

A prosthetic heart valve configured to be expanded between native leaflets of a native aortic annulus of a patient may include a collapsible and expandable stent, a cuff attached to the stent, and a plurality of prosthetic valve leaflets attached to the cuff. The stent may have a proximal end, a distal end, an annulus section adjacent the proximal end, and an aortic section adjacent the distal end. The stent may include a plurality of struts shaped to form a plurality of cells connected to one another in a plurality of annular rows around the stent. The stent may define a flow direction from the proximal end toward the distal end. The stent may have a minimum diameter in a direction perpendicular to the flow direction and a length in the flow direction between the proximal and distal ends when the stent is in an expanded use condition, the length being greater than the minimum diameter.

The plurality of prosthetic valve leaflets may be attached to the cuff between a first location and a second location distal to the first location in the flow direction. Each of the prosthetic valve leaflets may have a free edge. The entire free edge of each of the prosthetic valve leaflets may be located at least three-fifths of the length of the stent above the proximal end of the stent when the prosthetic valve leaflets are in an open position and the stent is in an expanded use condition.

A prosthetic heart valve configured to be expanded between native leaflets of a native aortic annulus of a patient may include a collapsible and expandable stent, a cuff attached to the stent, and a plurality of prosthetic valve leaflets attached to the cuff. The stent may have a proximal end, a distal end, an annulus section adjacent the proximal end, and an aortic section adjacent the distal end. The stent may include a plurality of struts shaped to form a plurality of cells connected to one another in a plurality of annular rows around the stent. The stent may define a flow direction from the proximal end toward the distal end.

The plurality of prosthetic valve leaflets may be attached to the cuff between a first location and a second location distal to the first location in the flow direction. Each of the prosthetic valve leaflets may have a free edge. The entire free edge of each of the prosthetic valve leaflets may be located at least about 25 mm above the proximal end of the stent when the prosthetic valve leaflets are in an open position and the stent is in an expanded use condition.

The entire free edge of each of the prosthetic valve leaflets may be located at least about 25 mm above the proximal end of the stent when the prosthetic valve leaflets are in the open position and the stent is in the expanded use condition. The entire free edge of each of the prosthetic valve leaflets may be located between about 25 mm and about 40 mm above the proximal end of the stent when the prosthetic valve leaflets are in the open position and the stent is in the expanded use condition. The stent may have a length between the distal end and the proximal end in the flow direction of no more than 50 mm in the expanded use condition. The stent may have a length between the distal end and the proximal end in the flow direction of between about 30 mm and about 50 mm in the expanded use condition.

The aortic section may have an expanded diameter greater than an expanded diameter of the annulus section. The annulus section of the stent may include three of the annular rows of cells and the aortic section of the stent may include one of the annular rows of cells. The rows of cells in the annulus section together may have a greater combined length in the flow direction than the row of cells in the aortic section when the stent is in the expanded use condition. When the prosthetic heart valve is expanded between the native leaflets of the native aortic annulus such that the proximal end of the stent is located below a proximal end of the native aortic annulus, and the prosthetic valve leaflets are in an open position, the entire free edge of each of the prosthetic valve leaflets may be located above a free edge of each of the native leaflets.

When the prosthetic heart valve is expanded between the native leaflets of the native aortic annulus such that the proximal end of the stent is located below a proximal end of the native aortic annulus, and the prosthetic valve leaflets are in an open position, the entire free edge of each of the prosthetic valve leaflets may be located at least 10 mm above a free edge of each of the native leaflets. When the prosthetic heart valve is expanded between the native leaflets of the native aortic annulus such that the proximal end of the stent is located below a proximal end of the native aortic annulus, and the prosthetic valve leaflets are in an open position, the entire free edge of each of the prosthetic valve leaflets may be located between about 10 mm and about 20 mm above a free edge of each of the native leaflets.

The cuff may have top and bottom edges and may occupy a first group of the cells, such that the cells above the top edge are open cells at least partially devoid of the cuff, and when the prosthetic heart valve is expanded between the native leaflets of the native aortic annulus such that the proximal end of the stent is located below a proximal end of the native aortic annulus, at least a portion of each of the open cells may be located above a free edge of each of the native leaflets. When the prosthetic heart valve is expanded between the native leaflets of the native aortic annulus such that the proximal end of the stent is located below a proximal end of the native aortic annulus, each of the open cells may be located entirely above the free edge of each of the native leaflets.

The aortic section of the stent may include struts that form a plurality of independent fingers. Each of the fingers may extend distally from a distal apex of a respective one of the cells to a free end. Each of the fingers may have a length of at least 8 mm. Each of the free ends may be spaced from the free ends of the other fingers. The aortic section of the stent may include a connecting element extending about a circumference of the prosthetic heart valve between the fingers. The connecting element may include a porous material configured to permit tissue ingrowth.

A method of expanding a prosthetic heart valve between native leaflets of a native aortic annulus of a patient may include collapsing the prosthetic heart valve into a catheter, inserting the catheter into a patient, advancing the catheter into the native aortic annulus, and expanding the prosthetic heart valve in a selected position between the native leaflets of the native aortic annulus such that the native leaflets are compressed between an exterior surface of the prosthetic heart valve and native aortic tissue such that the proximal end of the stent is located below a proximal end of the native aortic annulus, and the prosthetic valve leaflets move to an open position upon the flow of blood therethrough.

The prosthetic heart valve may include a stent, a cuff attached to the stent, and a plurality of prosthetic valve leaflets attached to the cuff. The stent may have a proximal end, a distal end, an annulus section adjacent the proximal end, and an aortic section adjacent the distal end. The stent may include a plurality of struts shaped to form a plurality of cells connected to one another in a plurality of annular rows around the stent. The stent may define a flow direction from the proximal end toward the distal end. The prosthetic valve leaflets may be attached to the cuff between a first location and a second location distal to the first location in the flow direction. Each of the prosthetic valve leaflets may have a free edge. The selected position may selected such that the free edges of the prosthetic valve leaflets are located above free edges of the native leaflets when the prosthetic valve leaflets are in the open position.

The cuff may include a proximal cuff and a distal cuff. The proximal cuff may be coupled to a first group of the plurality of struts adjacent a bottom edge of the proximal cuff and may be coupled to a bottom edge of the distal cuff at a top edge of the proximal cuff. The distal cuff may be coupled to a second group of the plurality of struts adjacent a top edge of the distal cuff. When blood flows through the prosthetic valve leaflets, some of the blood may flow through open cells that are distal to the cuff in the flow direction and at least partially devoid of the cuff, over the free edges of the native valve leaflets, and into the coronary sinus ostia of the patient.

The entire free edge of each of the prosthetic valve leaflets may be located at least 10 mm above the free edge of each of the native leaflets when the prosthetic valve leaflets are in the open position. The entire free edge of each of the prosthetic valve leaflets may be located at least 25 mm above the proximal end of the stent when the prosthetic valve leaflets are in the open position.

BRIEF DESCRIPTION OF THE DRAWINGS

Various embodiments of heart valves are disclosed herein with reference to the drawings, wherein.

Figure 1:
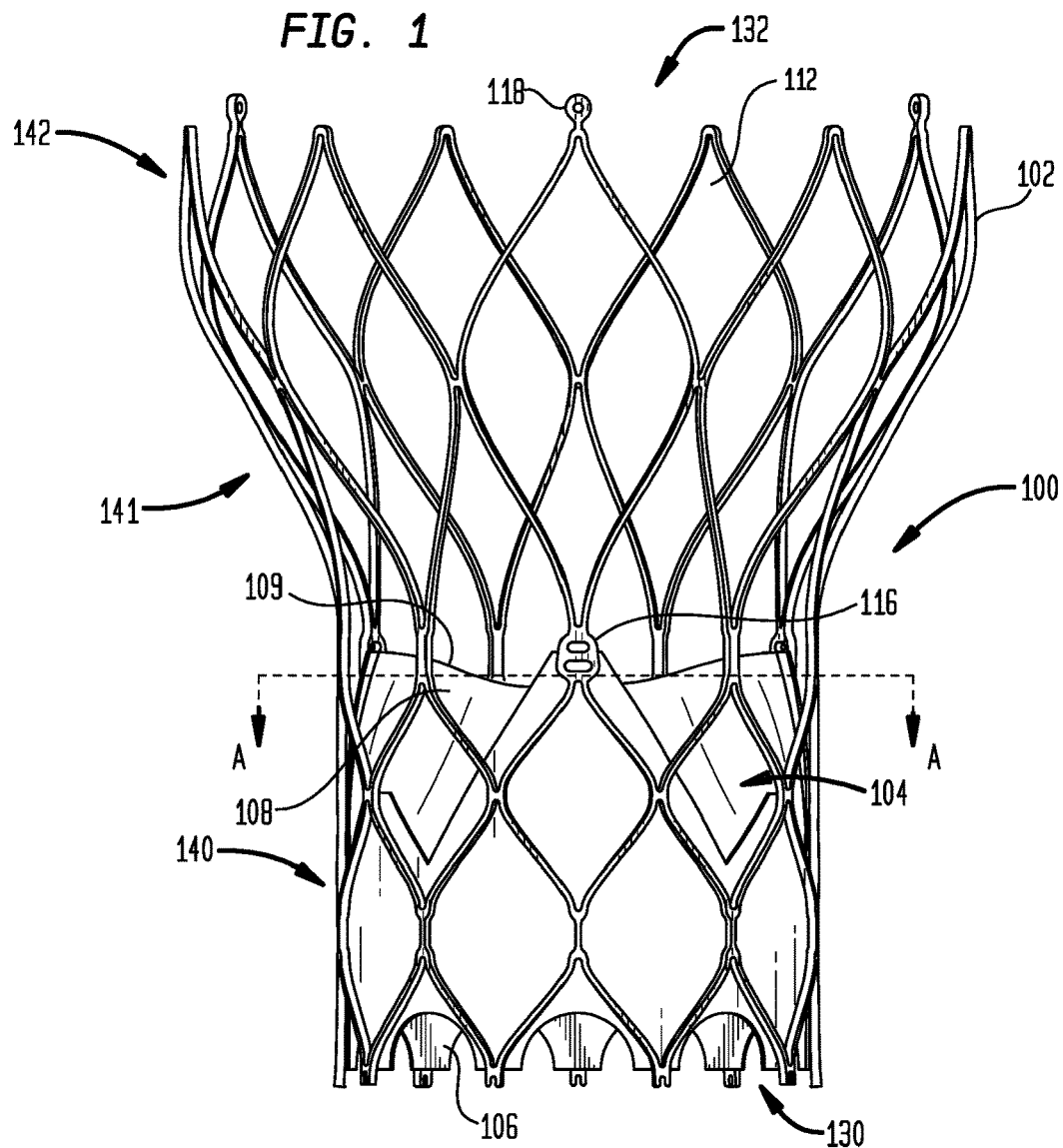
FIG. 1 is a side elevational view of a conventional prosthetic heart valve.

Various embodiments of the present invention will now be described with reference to the appended drawings. It is to be appreciated that these drawings depict only some embodiments of the invention and are therefore not to be considered limiting of its scope.

DETAILED DESCRIPTION

There is a need for further improvements to the devices, systems, and methods of manufacturing collapsible prosthetic heart valves, and in particular, self-expanding prosthetic heart valves having cuffs. Among other advantages, the present invention may address one or more of these needs.

Embodiments of the present invention may include a prosthetic heart valve configured to be expanded between native leaflets of a native aortic annulus of a patient, having a cuff having a landing zone extending over a greater distance in the flow direction than conventional prosthetic heart valves. For example, as will be described more fully below, the cuff landing zone may extend at least one-third of the length of the stent in the flow direction between a bottom edge of the cuff and a proximal end of a most proximal cell of the open cells when the stent is in the expanded use condition. In another example, the cuff landing zone may extend at least 16 mm in the flow direction between the bottom edge of the cuff and a proximal end of a most proximal cell of the open cells when the stent is in an expanded use condition.

Embodiments of the present invention may also include a prosthetic heart valve configured to be expanded between native leaflets of a native aortic annulus of a patient, having the entire free edge of each of the prosthetic valve leaflets located at a greater distance from a proximal end of the stent in the flow direction than conventional prosthetic heart valves, which may permit the entire free edge of each of the prosthetic valve leaflets to be located more supra-annular when installed in a native aortic annulus than prosthetic valve leaflets of conventional prosthetic heart valves. For example, as will be described more fully below, the entire free edge of each of the prosthetic valve leaflets may be located at least three-fifths of a length of the stent above the proximal end of the stent when the prosthetic valve leaflets are in an open position and the stent is in an expanded use condition. In another example, the entire free edge of each of the prosthetic valve leaflets may be located at least about 25 mm above the proximal end of the stent when the prosthetic valve leaflets are in the open position and the stent is in the expanded use condition.

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. When used to indicate relative locations within the aortic annulus, the aortic root, and the ascending aorta of a patient, the terms "above" and "below" are to be taken as relative to the juncture between the aortic annulus and the left ventricle. "Above" is to be understood as relatively farther from the left ventricle, and "below" is to be understood as relatively closer to the left ventricle. As used herein, the words "about" and "approximately" are intended to mean that slight variations from absolute are included within the scope of the value recited, for example, due to manufacturing tolerances.

Figure 6:
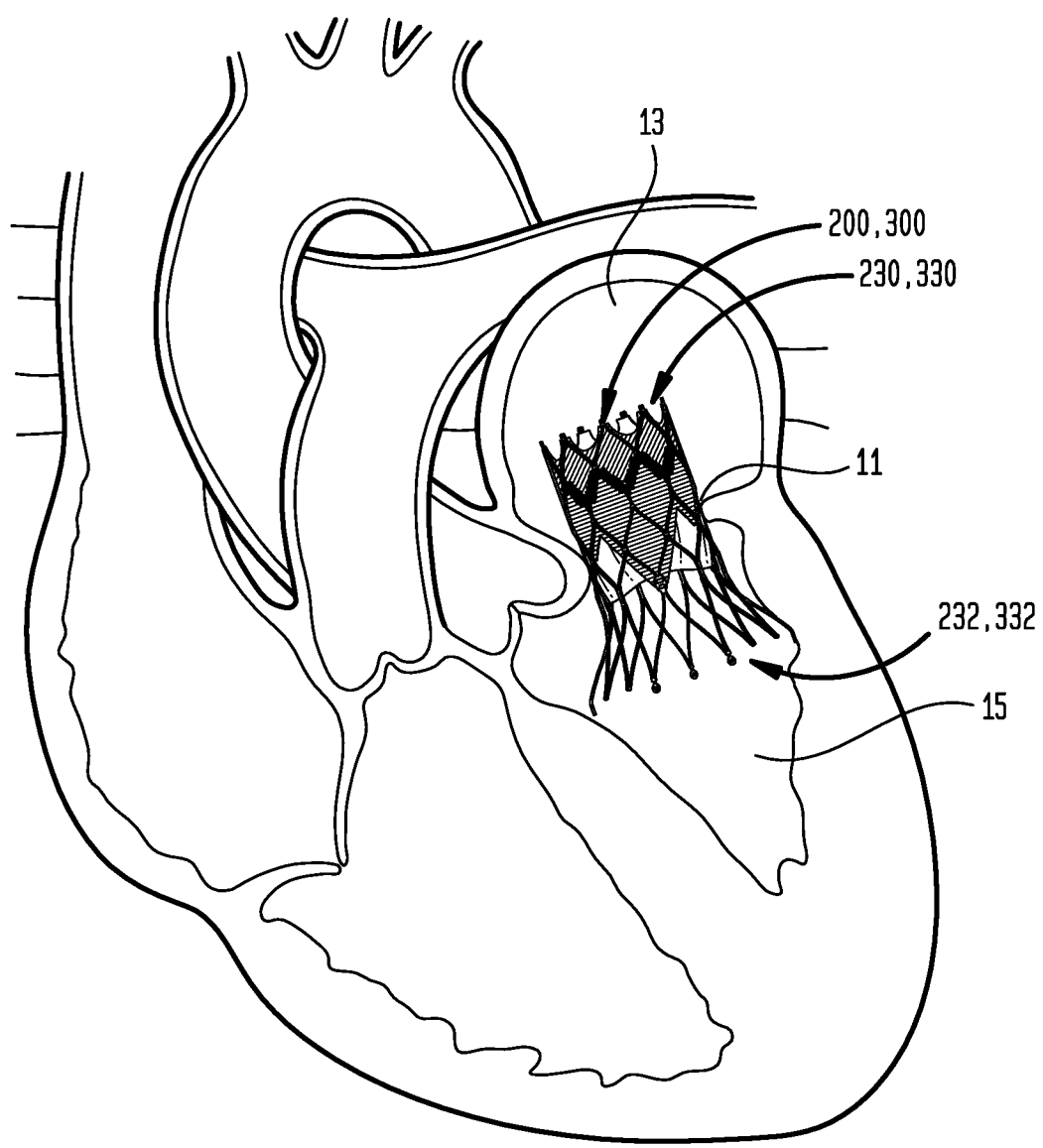
FIG. 6 is a side elevational view of the prosthetic heart valve of FIG. 4B or FIG. 5, shown in a deployed position within a native mitral annulus of a patient.

FIG. 1 shows one such collapsible stent-supported prosthetic heart valve 100 known in the art. The prosthetic heart valve 100 is designed to replace the function of a patient's native tricuspid, bicuspid, or unicuspid valve, such as a native aortic valve. It should be noted that while the inventions herein are described predominately in connection with their use with a prosthetic aortic valve and a stent generally having a shape as illustrated in FIG. 1, the inventions may also be used with bicuspid valves, such as the mitral valve (e.g., as shown in FIG. 6), and with stents having different shapes, such as those having a flared or conical annulus section, a less-bulbous aortic section, and the like, and a differently shaped transition section. Examples of collapsible prosthetic heart valves are described in International Patent Application Publication No. WO/2009/042196; U.S. Pat. Nos. 7,018,406; and 7,329,278, the disclosures of all of which are hereby incorporated herein by reference.

The prosthetic heart valve 100 will be described in more detail with reference to FIG. 1. The prosthetic heart valve 100 includes an expandable stent 102, which may be formed from biocompatible materials that are capable of self-expansion, such as, for example, shape memory alloys such as nitinol. The stent 102 extends from a proximal or annulus end 130 to a distal or aortic end 132. The stent 102 includes an annulus section 140 adjacent the proximal end 130 and an aortic section 142 adjacent the distal end 132. The annulus section 140 has a relatively small cross-section in the expanded condition, while the aortic section 142 has a relatively large cross-section in the expanded condition. Preferably, the annulus section 140 is in the form of a cylinder having a substantially constant diameter along its length, such as between about 12 mm and about 31 mm. A transition section 141 may taper outwardly from the annulus section 140 to the aortic section 142.

Each of the sections 140, 141, and 142 of the stent 102 includes a plurality of struts that are shaped to form a plurality of cells 112 connected to one another in one or more annular rows around the stent. For example, as shown in FIG. 1, the annulus section 140 may have two annular rows of complete cells 112, and the aortic section 142 and the transition section 141 may each have one or more annular rows of partial cells. The cells 112 in the aortic section 142 may be larger than the cells in the annulus section 140. The larger cells in the aortic section 142 may better enable the prosthetic valve 100 to be positioned in the native valve annulus without the stent structure interfering with blood flow to the coronary arteries.

The stent 102 may include one or more retaining elements 118 at the distal end 132 thereof, the retaining elements being sized and shaped to cooperate with female retaining structures (not shown) provided on a deployment device configured to deploy the prosthetic valve 100 in the native valve annulus of a patient. Examples of female retaining structures configured to receive the one or more retaining elements 118 of the stent 102 and delivery devices configured to deploy the prosthetic valve 100 may be found in U.S. Patent Application Publication No. US2012/0078350, which is hereby incorporated by reference herein.

The engagement of the retaining elements 118 with female retaining structures on the deployment device helps maintain the prosthetic heart valve 100 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and the heart valve deployed. In some variations, the retaining elements 118 may be disposed near the proximal end 130 of the prosthetic heart valve 100.

The prosthetic heart valve 100 also includes a valve assembly 104, preferably positioned in the annulus section 140 of the stent 102 and secured to the stent. The valve assembly 104 includes a cuff 106, and a plurality of leaflets 108 that collectively function as a one-way valve by coapting with one another. As a prosthetic aortic valve, the valve 100 has three leaflets 108. However, it will be appreciated that other prosthetic heart valves with which the stent structures of the present invention may be used may have a greater or lesser number of leaflets. The base of the leaflets 108 may be sutured to other structure of the valve 100. For example, this may result in securing the base of the leaflet through cuff material of the valve 100.

Although the cuff 106 is shown in FIG. 1 as being disposed on the luminal or inner surface of the annulus section 140, it is contemplated that the cuff may be disposed on the abluminal or outer surface of the annulus section, or the cuff may cover all or part of either or both of the luminal and abluminal surfaces. Both the cuff 106 and the leaflets 108 may be wholly or partly formed of any suitable biological material or polymer such as, for example, PTFE.

The leaflets 108 may be attached along their belly portions to the cells 112 of the stent 102, with the commissure between adjacent leaflets attached to commissure features 116 of the stent. Each leaflet 108 may have a free edge 109 that extends from a first commissure feature 116a to a second commissure feature 116b. The free edge 109 of each leaflet may have a first portion 109a that extends from the first commissure feature 116a to a triple point 107 where the three leaflets coapt, and a second portion 109b that extends from the triple point to the second commissure feature 116b. The first portion 109a and the second portion 109b together define the entire free edge 109.

As can be seen in FIG. 1, each commissure feature 116 may lie at the intersection of four cells 112 of the stent 102, two of the cells may be located adjacent one another in the same annular row, and the other two cells may be located in different annular rows and lie in end-to-end relationship. As shown in FIG. 1, the commissure features 116 may be positioned entirely within the annulus section 140 of the stent 102 or at the juncture of the annulus section and the transition section 141. The commissure features 116 may include one or more eyelets that facilitate the suturing of the leaflet commissures to the stent.

The prosthetic heart valve 100 may be used to replace a native aortic valve, a surgical heart valve, a repair device, or a heart valve that has undergone a surgical procedure. The prosthetic heart valve may be delivered to the desired site (e.g., near the native aortic annulus) using any suitable delivery device. During delivery, the prosthetic heart valve is disposed inside the delivery device in a collapsed condition. The delivery device may be introduced into a patient using a transfemoral, transapical, transseptal or any other percutaneous approach. Once the delivery device has reached the target site, the user may deploy the prosthetic heart valve 100 out of the delivery device. Upon deployment, the prosthetic heart valve 100 expands so that the annulus section 140 is in secure engagement within the native aortic annulus. When the prosthetic heart valve is properly positioned inside the heart, it works as a one-way valve, allowing blood to flow from the left ventricle of the heart to the aorta, and preventing blood from flowing in the opposite direction.

Figure 2:
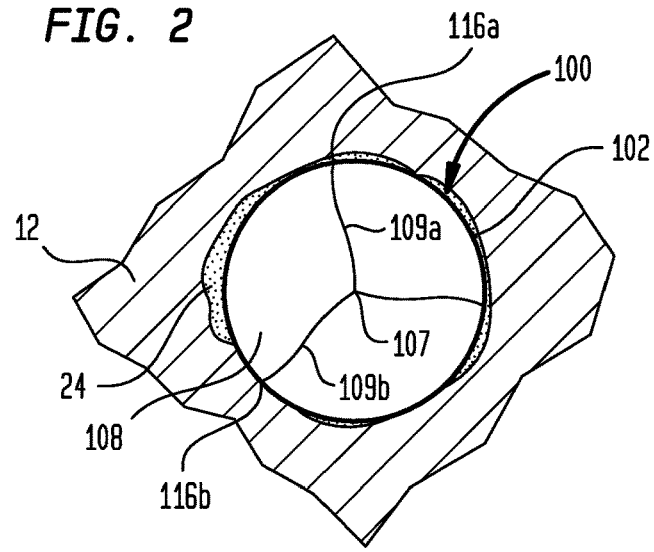
FIG. 2 is a highly schematic cross-sectional view taken along line A-A of FIG. 1 and showing the prosthetic heart valve disposed within a native valve annulus.

FIG. 2 is a highly schematic cross-sectional illustration of the prosthetic heart valve 100 disposed within a native valve annulus 12. As seen in FIG. 2, the annulus section 140 of the stent 102 has a substantially circular cross-section that is disposed within the non-circular native valve annulus 12. At certain locations around the perimeter of the heart valve 100, crescent-shaped gaps 24 form between the heart valve and native valve annulus 12. Blood flowing through these gaps and past the valve assembly 104 of the prosthetic heart valve 100 may cause regurgitation and other inefficiencies that reduce cardiac performance. Such improper fitment may be due to suboptimal native valve annulus geometry due, for example, to calcification of the native valve annulus 12 or to unresected native leaflets.

Figure 3A:
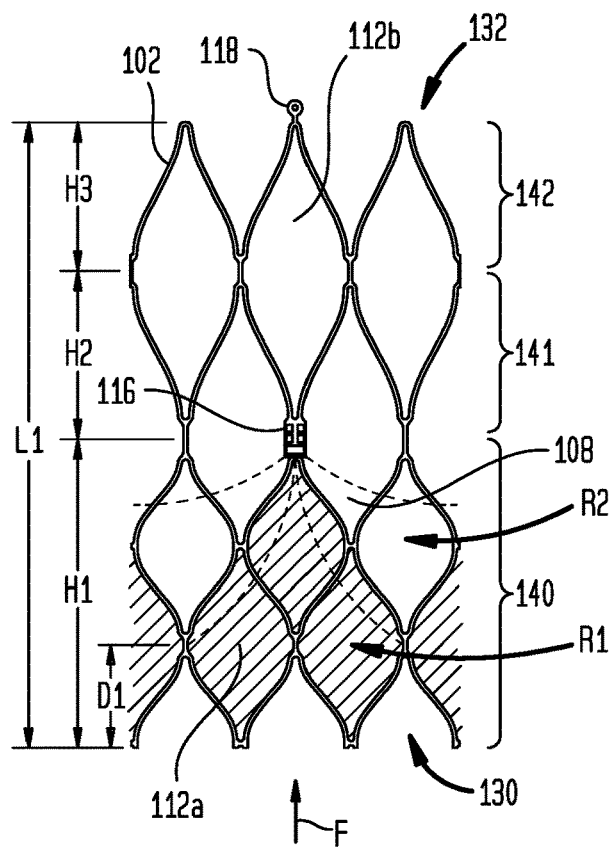
FIG. 3A is a developed view of a portion of the stent of FIG. 1.

FIG. 3A shows a developed view of a portion of the stent 102 of valve 100. As can be seen in FIG. 3A, annulus section 140 extends a length H1 in the flow direction F of about 1.5 times the height of an annulus cell 112a. The transition section 141 extends a length H2 in the flow direction F of about 0.5 times the height of an aortic cell 112b, and the aortic section 142 extends a length H3 in the flow direction F of about 0.5 times the height of an aortic cell. The stent 102 extends a total length L1 in the flow direction F. L1 may preferably be no longer than 50 mm, more preferably between about 30 mm and about 50 mm. As shown in FIG. 3A, the commissure features 116 may be positioned at the juncture of the annulus section 140 and the transition section 141, at a distance H1 from the proximal end 130 of the stent 102.

The leaflets 108 may be attached to the first and second annular rows of cells R1, R2 of the stent 102 beginning a distance D1 from the proximal end 130 of the stent (approximately 0.5 times the height of an annulus cell 112a), and extending in the flow direction F to the commissure features 116.

Figure 3B:
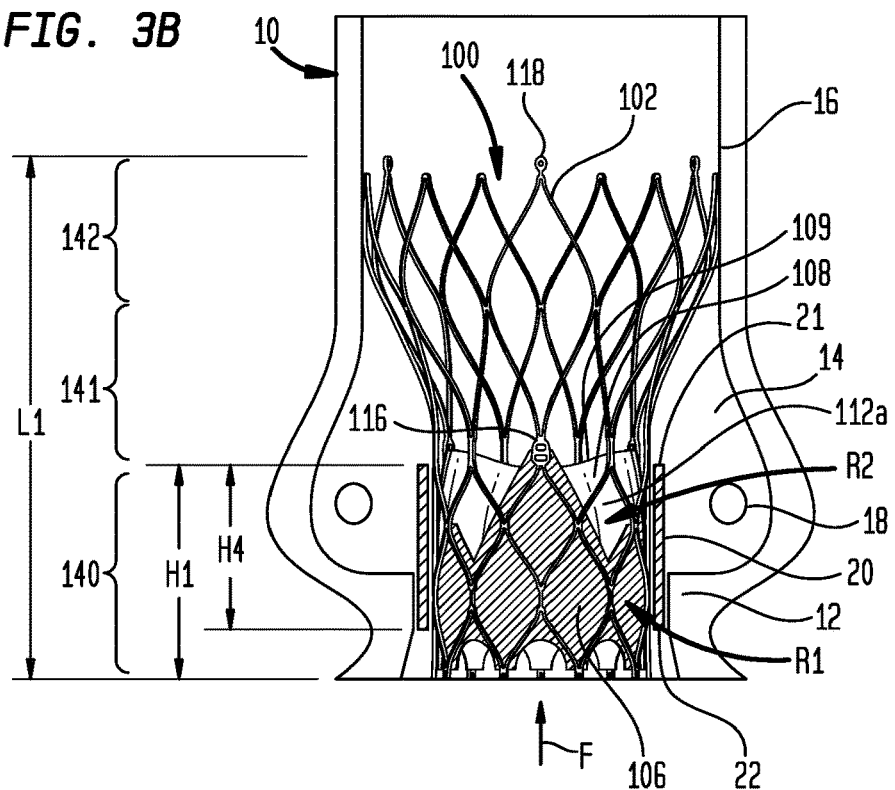
FIG. 3B is a side elevational view of the prosthetic heart valve of FIG. 1 shown in a deployed position within a native aortic annulus and aortic root of a patient.

FIG. 3B shows the prosthetic valve 100 deployed in an aorta 10 of a patient, with the annulus section 140 of the stent 102 disposed at the native valve annulus 12, the aortic section 142 contacting the ascending aorta 16, and the transition section 141 extending across a portion of the aortic root 14. When the prosthetic valve 100 is deployed in the aorta 10, the native valve leaflets 20 are compressed against the native valve annulus 12 outside of the prosthetic valve.

It can be seen in FIG. 3B that in some patients, the free edges 21 of the compressed native valve leaflets 20 may extend to a height H4 in the flow direction F below which almost all of the annulus section 140 of the stent 102 is located once the valve 100 is deployed in the aorta 10, such that one or more of the annulus cells 112a (i.e., open cells) that are not filled with material of the tissue cuff 106 (e.g., two-thirds of the cells within the second row R2) may be located at least partially below the free edges of the compressed valve leaflets. As shown in FIG. 3B, one or more of the open annulus cells 112a may be located entirely below the free edges of the compressed valve leaflets. Having one or more of the open annulus cells 112a located at least partially below the free edges of the compressed valve leaflets may occur either due to the design of the valve 100 or to deploying the valve relatively low, such that the proximal end 130 of the valve extends into the left ventricle.

In some circumstances, some of the blood that flows through the leaflets 108 and through the open cells 112a may be impeded by the compressed native valve leaflets 20 that abut the open cells. As a result, some of the impeded blood may flow against the compressed native valve leaflets 20 and down between the native leaflets and the exterior of the valve 100 back into the left ventricle, for example, through the gaps 24 shown in FIG. 2. Such flow may cause regurgitation and other inefficiencies that may reduce cardiac performance, and may reduce blood flow into the coronary sinus ostia 18.

Figure 4A:
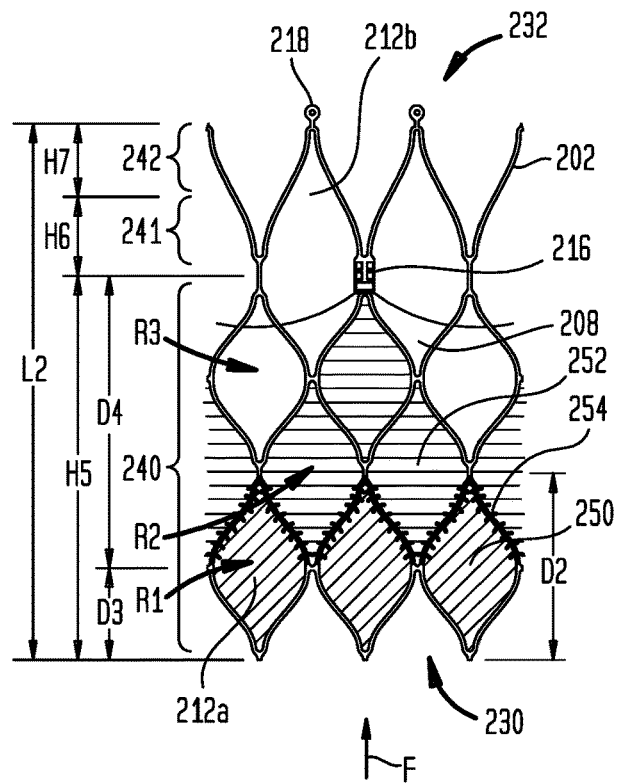
FIG. 4A is a developed view of a portion of a stent according to an embodiment of the invention.
Figure 4B:
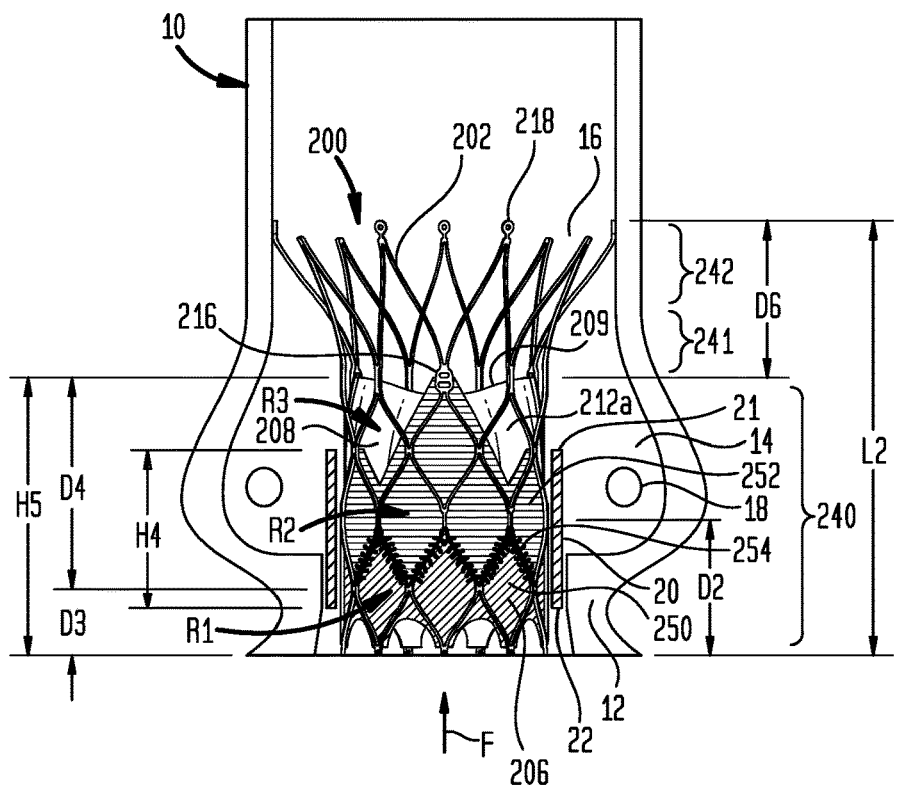
FIG. 4B is a side elevational view of a prosthetic heart valve including the stent of FIG. 4B, shown in a deployed position within a native aortic annulus and aortic root of a patient.

FIG. 4A shows a developed view of a portion of a stent 202 of a valve 200 (FIG. 4B). As can be seen in FIG. 4A, the annulus section 240 extends a length H5 in the flow direction F of about two times the height of an annulus cell 212a. The transition section 241 extends a length H6 in the flow direction F of about 0.25 times the height of an aortic cell 212b, and the aortic section 242 extends a length H7 in the flow direction F of about 0.25 times the height of an aortic cell. The stent 202 (or the stent 302 described below) extends a total length L2 in the flow direction F. L2 may preferably be no longer than 50 mm, more preferably between about 30 mm and about 50 mm. As shown in FIG. 4A, the commissure features 216 may be positioned at the juncture of the annulus section 240 and the transition section 241, at a distance H5 from the proximal end 230 of the stent 202. When the stent 202 (or the stent 302) is in an expanded use condition, the stent may have a minimum diameter in a direction perpendicular to the flow direction between about 20 mm and about 25 mm, preferably about 23 mm. When the stent 202 (or the stent 302) is in an expanded use condition, the length L2 may be greater than the minimum diameter of the stent.

The annulus section 240 of the stent 202 may include three annular rows of cells 212a, and the aortic section 242 of the stent may include one annular row of cells 212b, the row of cells in the aortic section having a greater length in the flow direction F than each of the rows of cells in the annulus section. The rows of cells in the annulus section 240 together may have a greater combined length in the flow direction F than the row of cells in the aortic section 242.

The stent 202 may include one or more retaining elements 218 at the distal end 232 thereof, the retaining elements being sized and shaped to cooperate with female retaining structures (not shown) provided on a deployment device configured to deploy the prosthetic valve 200 in the native valve annulus 12 of a patient. As can be seen in FIG. 4A, the stent 202 may include a retaining element 218 extending distally from the apex of each of the aortic cells 212b that has one of its struts extending through a commissure feature 216.

Compared to the retaining elements 118 of FIG. 3A, the retaining elements 218 of FIG. 4A may be larger and may have a greater radius of curvature, which may help prevent the retaining elements from eventually migrating to penetrate the wall of the ascending aorta after the valve 200 has been deployed into the patient. For example, the retaining elements 118 of FIG. 3A may have a radius between about 1.0 mm and about 1.8 mm, and the retaining elements 218 of FIG. 4A may have a radius between about 1.8 mm and about 3.0 mm.

The leaflets 208 may be attached to second and third rows of cells R2, R3 of the stent 202 beginning a distance D2 from the proximal end 230 of the stent (approximately equal to the height of an annulus cell 212a), and extending in the flow direction F to the commissure features 216.

FIG. 4B shows the prosthetic valve 200 deployed in an aorta 10 of a patient, with the annulus section 240 of the stent 202 disposed at the native valve annulus 12, the aortic section 242 contacting the ascending aorta 16, and the transition section 241 extending across a portion of the aortic root 14. When the prosthetic valve 200 is deployed in the aorta 10, the native valve leaflets 20 are compressed against the native valve annulus 12 outside of the prosthetic valve. The expanded diameter of the annulus section 240 of the stent 202 may preferably be between about 12 mm and about 31 mm.

It can be seen in FIG. 4B that in some patients, the free edges 21 of the compressed native valve leaflets 20 may extend to height H4 in the flow direction F. Since the annulus section 240 of the stent 202 is longer than the annulus section 140 of the stent 102, a larger portion of the annulus section 240 may extend above the height H4 compared to the annulus section 140, such that one or more of the cells 212a that are at least partially devoid of material of the tissue cuff 206 (e.g., two-thirds of the cells within the third row R3) may be located above the free edges of the compressed valve leaflets. The longer annulus section 240 compared to the annulus section 140, and the longer cuff 206 compared to the cuff 106, may provide a user a broader range for positioning the valve 200 relative to the native aortic annulus while still providing an effective seal between the cuff 206 and the native aortic annulus and native leaflets 20.

For example, a landing zone (i.e., continuous cylindrical portion) of the cuff 206 may extend over a length of about 16 mm to about 18 mm in the flow direction F between the proximal end 230 of the stent 202 and the lowest open cell 212a, compared to a landing zone of about 8 mm to about 10 mm for the cuff 106, when the stent is in an expanded use condition. The landing zone may extend over a length of at least 12 mm in the flow direction F, preferably at least 14 mm, more preferably at least 16 mm, and most preferably at least 18 mm, when the stent 202 is in an expanded use condition. The landing zone may extend over a length of at least one-third of the length L2 of the stent 202 in the flow direction F. The entire free edge 209 of each of the prosthetic valve leaflets 208 may be located within a distance D6 in the flow direction F from the distal end 232 of the stent 202 when the prosthetic valve leaflets are in the open position and the stent is in the expanded use condition, the distance D6 being less than a length of the landing zone in the flow direction. In such an embodiment, D6 may be about 13 mm, for example, and the landing zone may be about 16 mm.

As used herein, a stent 102, 202, or 302 is in an "expanded use condition" when the stent is radially expanded between native leaflets of the native aortic annulus, or radially expanded to the same extent as it would be between native leaflets of the native aortic annulus. All dimensions in the flow direction as described herein are to be taken when the stent is in an expanded use condition.

In the example shown in FIG. 4B, the entire free edge 209 of each of the prosthetic valve leaflets 208 may be located above the free edge 21 of each of the compressed native valve leaflets 20 when the prosthetic valve leaflets are in an open position (i.e., allowing blood to flow therethrough). For example, the entire free edge 209 of each of the prosthetic valve leaflets 208 may be located at least 10 mm above the free edge 21 of each of the compressed native valve leaflets 20, preferably between about 10 mm and about 20 mm above the free edge of each of the compressed native valve leaflets. The entire free edge 209 of each of the prosthetic valve leaflets 208 may be located at least 25 mm above the proximal end 230 of the stent 202 when the prosthetic valve leaflets are in the open position, preferably between about 25 mm and about 40 mm above the proximal end of the stent. The entire free edge 209 of each of the prosthetic valve leaflets 208 may be located at least three-fifths of the length of the stent 202 above the proximal end 230 of the stent when the prosthetic valve leaflets are in the open position.

As can be seen by comparing FIGS. 3A and 4A, when the prosthetic valve leaflets are in an open position, the entire free edge 209 of each of the leaflets 208 is located higher than each of the free edges 109 of the leaflets 108, which may permit the valve 200 to have better blood flow to the coronary sinus ostia 18 than the valve 100. In some circumstances, most or all of the blood that flows through the leaflets 208 and through the open cells 212a may flow above the free edges 21 of the native valve leaflets 20, and thereby not be impeded by the native valve leaflets. As such, the blood may have an improved flow path to the coronary sinus ostia 18, which may help prevent regurgitation and other inefficiencies that may reduce cardiac performance. When deployed in the aorta 10, the valve 200 having open annulus cells 212a above the free edges 21 of the compressed native valve leaflets 20 may produce less regurgitation than the valve 100.

One potential way to achieve the result of the entire free edges of the leaflets of prosthetic valve 100 being located above the free edges 21 of the compressed valve leaflets 20 would be to deploy the valve higher in the aorta, that is, farther away from the left ventricle. However, positioning the proximal end of the stent 130 too high relative to the native aortic annulus 12 is not desirable because a valve deployed in this position may only contact a small portion of the native aortic annulus, thereby making the valve more difficult to position and more prone to migration as the native aortic annulus would not be able to effectively grip the prosthetic valve. It is preferable that the proximal end of the stent 130 be placed no higher than the lowest portion of the native aortic annulus 12 (i.e., the portion that is closest to the left ventricle).

The valves 200 and 300 described herein may achieve the result of the free edges of the prosthetic leaflets being located above the free edges 21 of the compressed valve leaflets 20 when the prosthetic valve leaflets are in an open position, while at the same time lengthening the annulus section of the prosthetic valve relative to conventional prosthetic valves so that the native aortic annulus 12 can effectively grip the prosthetic valve.

The length L2 of the valve 200 (FIG. 4B) is less than the length L1 of the valve 100 (FIG. 3B), such that the valve 200 extends a shorter distance from the proximal end 22 of the aortic annulus 12 than the valve 100. Because the valve 200 when deployed does not extend as far into the ascending aorta as the valve 100, the valve 200 may avoid contacting weaker sections of the ascending aorta in patients having atypical morphology of the aortic root and ascending aorta compared to a typical patient (e.g., patients having aortic insufficiency, relatively young patients, and patients having bicuspid or monocuspid native aortic valves), which may help prevent aortic dissection in such atypical patients.

The cuff 206 shown in FIGS. 4A and 4B may include a proximal cuff 250 and a distal cuff 252. The proximal cuff 250 and the distal cuff 252 may either be proximal and distal portions of a single unitary cuff, or the proximal and distal cuffs may be initially separate from one another and coupled together along a boundary line by stitching, for example.

Each of the cuffs 250 and 252 may be disposed on the luminal or inner surface of the annulus section 240, the abluminal or outer surface of the annulus section, or the cuffs may each cover all or part of either or both of the luminal and abluminal surfaces. Each of the cuffs 250 and 252 may be wholly or partly formed of any suitable biological material or polymer or suitable combination thereof such as, for example, PTFE, PET, or ultra high molecular weight polyethylene (UHMWPE).

The proximal cuff 250 and the distal cuff 252 may be made from different materials. The cuff 206 may include a thinner material in the distal cuff 252 region that will add as little bulk as possible to the space occupied by the leaflets 208 so as to minimize the crimped diameter of that portion of the cuff. The cuff 206 may include a thicker and/or expandable material in the proximal cuff 250 region that does not significantly overlap with the leaflets 208, so that improved sealing against the native annulus 12 may be obtained with no impact or a minimal impact on the crimped diameter of the cuff. The proximal cuff 250 may have a first average thickness in a radial direction perpendicular to the flow direction F, and the distal cuff 252 may have a second average thickness in the radial direction, the first average thickness being greater than the second average thickness.

The proximal cuff 250 may be made of or may include a relatively porous material that is suitable for tissue ingrowth from the native annulus and/or sealing against the native annulus 12, such as a woven or braided fabric material. For example, the proximal cuff 250 may incorporate polyvinyl alcohol (PVA), PET, UHMWPE, felt-like fabric, foam shape memory portions, or a sponge-like portion into the material of the cuff. The proximal cuff 250 may include radiopaque fiber woven into a base material of the proximal cuff, or one or more sections of the proximal cuff may be radiopaque. The proximal cuff 250 may be formed from a porous membrane embedded with microspheres that may swell in size when exposed to blood after the valve 200 has been deployed in the aorta 10. The enlarged cuff may then fill the gaps (e.g., the gaps 24) between the native valve annulus 12 and the prosthetic heart valve 200, minimizing or preventing perivalvular leakage. Other examples of suitable porous and/or expanding materials for the proximal cuff 250 may be found in co-pending and co-owned U.S. patent application Ser. No. 13/829,036, which is hereby incorporated herein by reference. Furthermore, as shown in FIG. 4B, the proximal cuff 250 and the distal cuff 252 may have different fiber orientations to customize the strength and/or wear resistance of the proximal cuff and the distal cuff in particular directions relative to the native annulus 12.

As can be seen in FIG. 4B, the proximal cuff 250 extends from the proximal end 230 of the stent 202 across the distance D2 in the flow direction F (approximately equal to the height of an annulus cell 212a), such that the proximal cuff and the leaflets 208 have either no overlap or a small amount of overlap in the flow direction. The proximal cuff 250 may extend into the first annular row R1 of complete cells 212a adjacent the proximal end 230 of the stent 202.

The distal cuff 252 may be made of or may include a relatively thin, less porous, and abrasion resistant material that is suitable for protecting the leaflets 208 from abrasion while permitting the valve 200 to have as small a diameter as possible while in a radially collapsed position in a delivery device. For example, the distal cuff 252 may be made of or may include a synthetic material such as polyester, PFTE, PET, UHMWPE, electrospun materials (e.g., electrospun collagen or fibrin), collagen-impregnated PET, or a suitable combination thereof. The distal cuff 252 material may be in the form of one or more sheets, rather than a woven or braided fabric. The distal cuff 252 may also include one or more sections of radiopaque material. Such synthetic materials may enable a thinner distal cuff 252 to be produced, resulting in a lower crimped diameter for the valve 200, as well as the need for less force for loading and resheathing. The use of synthetic materials may also increase the durability and life expectancy of the distal cuff 252. Other examples of suitable thin and durable materials for the distal cuff 252 may be found in co-pending and co-owned U.S. patent application Ser. No. 13/829,036.

As can be seen in FIG. 4B, the distal cuff 252 may be attached to the stent 202 beginning a distance D3 from the proximal end 230 of the stent (approximately 0.5 times the height of an annulus cell 212a), and may extend in the flow direction F to the commissure features 216, for a total distance D4 (approximately 1.5 times the height of an annulus cell 212a). The distal cuff 252 may extend into the second annular row R2 of complete cells 212a and may also extend into some cells of the third annular row R3 of complete cells 212a. Two-thirds of the annulus cells 212a of this third annular row R3 may be unoccupied or only partially occupied by material of the distal cuff 252, so that blood may flow through these unoccupied annulus cells to the coronary sinus ostia 18. The distal cuff 252 preferably extends into those annulus cells 212a of the third annular row R3 immediately below the commissure features 216.

The distal cuff 252 may be sutured to the proximal cuff 250 along a boundary line 254 that extends along the border between adjacent rows of complete annulus cells 212a. At least a portion of the distal cuff 252 may extend across the same portion of the stent 202 in the flow direction F as the leaflets 208, such that the location of the distal cuff in the flow direction partially overlaps the location of the leaflets.

Figure 5:
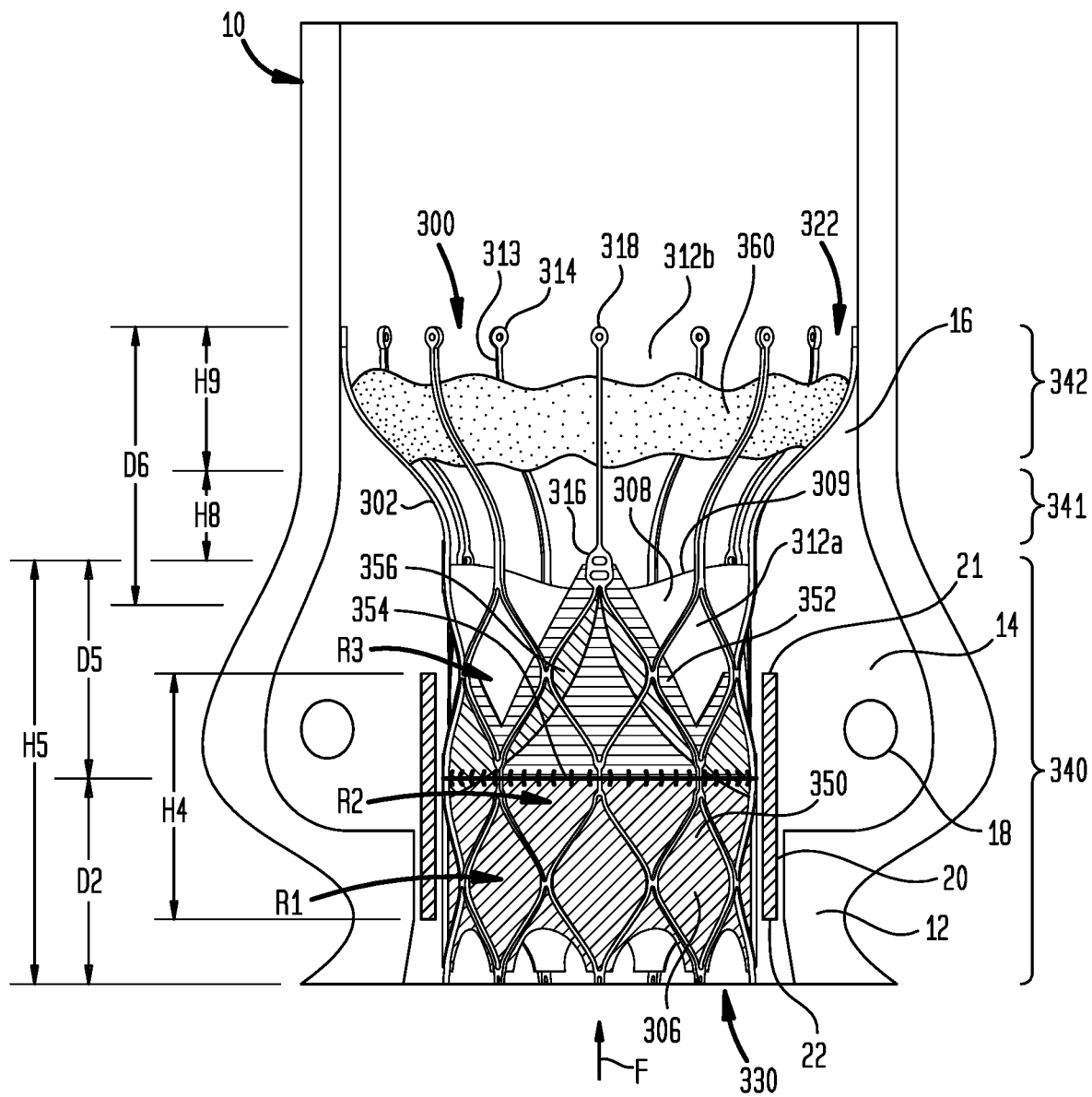
FIG. 5 is a side elevational view of a prosthetic heart valve according to another embodiment, shown in a deployed position within a native aortic annulus and aortic root of a patient.

FIG. 5 shows a prosthetic valve 300 deployed in the aorta 10 of a patient, with the annulus section 340 of the stent 302 disposed at the native valve annulus 12, the aortic section 342 contacting the ascending aorta 16, and the transition section 341 extending across a portion of the aortic root 14. Similar to FIGS. 3B and 4B, when the prosthetic valve 300 is deployed in the aorta 10, the native valve leaflets 20 are compressed against the native valve annulus 12 outside of the prosthetic valve.

As can be seen in FIG. 5, the annulus section 340 extends a length H5 in the flow direction F of two times the height of an annulus cell 312a. The transition section 341 extends a length H8 in the flow direction F, and the aortic section 342 extends a length H9 in the flow direction F. The commissure features 316 may be positioned at the juncture of the annulus section 340 and the transition section 341, at a distance H5 from the proximal end 330 of the stent 302. Rather than comprising complete cells 312 or parts of complete cells, the transition section 341 and the aortic section 342 comprise portions of independent fingers 313, each finger extending distally from the apex of a respective one of the annulus cells 312a in the most distal row of cells. Each finger 313 preferably may extend distally at least 5 mm from the apex of a respective one of the annulus cells 312a in the most distal row of cells, more preferably at least 8 mm, most preferably at least 10 mm. Each finger 313 may have a free end 314 that is not connected to the free end of any of the other fingers.

The stent 302 may include one or more retaining elements 318 at the distal end 332 thereof, the retaining elements being sized and shaped to cooperate with female retaining structures (not shown) provided on a deployment device configured to deploy the prosthetic valve 300 in the native valve annulus 12 of a patient. The retaining elements 318 may be either the retaining elements 118 of FIGS. 3A and 3B or the retaining elements 218 of FIGS. 4A and 4B.

Similar to the leaflets 208 shown in FIG. 4B, the leaflets 308 of the prosthetic valve may be attached to the second and third rows of cells R2, R3 of the stent 302 beginning slightly below a distance D2 from the proximal end 330 of the stent (approximately equal to the height of an annulus cell 312a) and extending in the flow direction F to the commissure features 316.

Similar to FIG. 4B, in some patients, the free edges 21 of the compressed native valve leaflets 20 may extend to height H4 in the flow direction F. Since the annulus section 340 of the stent 302 is longer than the annulus section 140 of the stent 102, a larger portion of the annulus section 340 may extend above the height H4 compared to the annulus section 140, such that one or more of the cells 312a that are at least partially devoid of material of the tissue cuff 306 may be located above the free edges of the compressed valve leaflets. The longer annulus section 340 compared to the annulus section 140, and the longer cuff 306 compared to the cuff 106, may provide a user a broader range for positioning the valve 300 relative to the native aortic annulus while still providing an effective seal between the cuff 306 and the native aortic annulus and native leaflets 20.

For example, a landing zone (i.e., continuous cylindrical portion) of the cuff 306 may extend over a length of about 16 mm to about 18 mm between the proximal end 330 of the stent 302 and the lowest open cell 312a, compared to a landing zone of about 8 mm to about 10 mm for the cuff 106. The landing zone may extend over a length of at least one-third of the length of the stent 302 in the flow direction F. The entire free edge 309 of each of the prosthetic valve leaflets 308 may be located within a distance D6 in the flow direction F from the distal end 332 of the stent 302 when the prosthetic valve leaflets are in the open position and the stent is in the expanded use condition, the distance D6 being less than a length of the landing zone in the flow direction. In such an embodiment, D6 may be about 13 mm, for example, and the landing zone may be about 16 mm.

In the example shown in FIG. 5, the entire free edge 309 of each of the prosthetic valve leaflets 308 may be located above the free edge 21 of each of the compressed native valve leaflets 20 when the prosthetic valve leaflets are in an open position. For example, the entire free edge 309 of each of the prosthetic valve leaflets 308 may be located at least 10 mm above the free edge 21 of each of the compressed native valve leaflets 20, preferably between about 10 mm and about 20 mm above the free edge of each of the compressed native valve leaflets. The entire free edge 309 of each the prosthetic valve leaflets 308 may be located at least 25 mm above the proximal end 330 of the stent 302 when the prosthetic valve leaflets 308 are in the open position, preferably between about 25 mm and about 40 mm above the proximal end of the stent. The entire free edge 309 of each of the prosthetic valve leaflets 308 may be located at least three-fifths of the length of the stent 302 above the proximal end 330 of the stent when the prosthetic valve leaflets are in the open position.

In such an example, similar to the valve 200, some of the blood that flows through the leaflets 308 may flow through the open cells 312a, over the free edges 21 of the compressed native valve leaflets 20 into the aortic root 14, and into the coronary sinus ostia 18. This flow pattern may be desirable because there may be an unimpeded flow of blood through the open cells 312a over the free edges 21 of the native leaflets 20 to the coronary sinus ostia 18, compared to the valve 100 in certain situations, in which the flow of blood through the open cells 112a may be impeded by the native leaflets that abut the open cells.

The cuff 306 shown in FIG. 5 may include a proximal cuff 350 and a distal cuff 352. The proximal cuff 350 and the distal cuff 352 may either be proximal and distal portions of a single unitary cuff, or the proximal and distal cuffs may be initially separate from one another and coupled together along a boundary line by stitching, for example. Each of the cuffs 350 and 352 may be disposed on the luminal or inner surface of the annulus section 340, the abluminal or outer surface of the annulus section, or the cuffs may each cover all or part of either or both of the luminal and abluminal surfaces. Each of the cuffs 350 and 352 may be wholly or partly formed of any suitable biological material or polymer such as, for example, PTFE.

The proximal cuff 350 and the distal cuff 352 may be made from different materials. Similar to the cuff 206, the cuff 306 may include a thinner material in the region of the distal cuff 352 that will add as little bulk as possible to the space occupied by the leaflets 308 so as to minimize the crimped diameter of that portion of the prosthetic valve. The cuff 306 may include a thicker and/or expandable material in region of the proximal cuff 350 that does not significantly overlap with the leaflets 308, so that improved sealing against the native annulus 12 may be obtained with no impact or a minimal impact on the crimped diameter of the cuff. The proximal cuff 350 may be made of or may include any of the materials described above with reference to the proximal cuff 250, and the distal cuff 352 may be made of or may include any of the materials described above with reference to the distal cuff 252.

As can be seen in FIG. 5, the proximal cuff 350 extends from the proximal end 330 of the stent 302 across the distance D2 in the flow direction F (approximately equal to the height of an annulus cell 312a), such that the proximal cuff and the leaflets 308 have either no overlap or a small amount of overlap in the flow direction. The proximal cuff 350 may extend into the first annular row R1 of complete cells 312a adjacent the proximal end 330 of the stent 302 and into the proximal half of the second annular row R2 of complete cells.

The distal cuff 352 may be attached to the stent 302 beginning a distance D2 from the proximal end 330 of the stent, extending in the flow direction F to the commissure features 316, for a total distance D5 (approximately equal to the height of an annulus cell 312a). The distal cuff 352 may extend into the distal half of the second annular row R2 of complete cells 312a and may also extend into some cells of the third annular row R3 of complete cells 312a. Two-thirds of the annulus cells 312a of this third annular row R3 may be unoccupied or only partially occupied by material of the distal cuff 352, so that blood may flow through these unoccupied annulus cells to the coronary sinus ostia 18. The distal cuff 352 preferably extends into those annulus cells 312a of the third annular row immediately below the commissure features 316.

As shown in FIG. 5, the proximal cuff 350 may have a cylindrical shape that joins the distal cuff 352 in a substantially circular closed curve, the curve lying in a plane generally perpendicular to the flow direction as opposed to the zig-zag configuration of the boundary between the proximal and distal cuffs 250 and 252 shown in FIGS. 4A and 4B. The distal cuff 352 may be sutured to the proximal cuff 350 along a boundary line 354 that extends in a closed curve annularly about the circumference of the stent 302. At least a portion of the distal cuff 352 may extend across the same portion of the stent 302 in the flow direction F as the leaflets 308, such that the location of the distal cuff in the flow direction partially overlaps the location of the leaflets.

The distal cuff 350 may have pockets 356 that may be formed from a porous membrane embedded with microspheres that may swell in size when exposed to blood after the valve 300 has been deployed in the aorta 10. The enlarged pockets 356 may then help fill the gaps (e.g., the gaps 24) between the native valve annulus 12 and the prosthetic heart valve 300, minimizing or preventing perivalvular leakage. The proximal edge of the pockets 356 may form a parabolic pattern that approximately follows the locations at which the leaflets 308 are sutured to the stent 302 and/or the cuff 306. Other examples of suitable porous and/or expanding materials for the pockets 356 and potential shapes and configurations of the pockets may be found in co-pending and co-owned U.S. patent application Ser. No. 13/829,036.

Because the transition section 341 and the aortic section 342 comprise portions of independent fingers 313 that do not form closed cells like the aortic cells 112b and 212b described above, the transition and aortic sections of the valve 300 may be less resistant to deflection in a radial direction R that is generally perpendicular to the flow direction F. That is, when deployed, the aortic section 342 of the stent 302 may apply a lower radially-expansive force against a portion of the ascending aorta than the aortic section 142 of the stent 102 or the aortic section 242 of the stent 202. Therefore, the aortic section 342 of the valve 300 may be less likely to penetrate weaker sections of the ascending aorta in patients having atypical morphology of the aortic root and ascending aorta compared to a typical patient (e.g., patients having aortic insufficiency, relatively young patients, and patients having bicuspid or monocuspid native aortic valves), which may help prevent aortic dissection in such atypical patients.

The valve 300 may optionally include a connecting element 360 extending about the circumference of the valve between the independent fingers 313 in the aortic section 342. The connecting element 360 may be made of or may include a relatively porous material that is suitable for tissue ingrowth from the ascending aorta 16, such as a fabric material, for example. Such a connecting element 360 may help reinforce weaker sections of the ascending aorta in patients having atypical morphology of the aortic root and ascending aorta compared to a typical patient, which may help prevent aortic dissection in such atypical patients.

Although the proximal cuff 350 and the distal cuff 352 are shown in FIG. 5 and described as being joined along a boundary line 354 that extends in a closed curve extending annularly about the circumference of the stent 302 in a plane generally perpendicular to the flow direction, that need not be the case. The cuff 306 may alternatively include the proximal cuff 250 and the distal cuff 252 described above with respect to FIGS. 4A and 4B as having a zig-zag shaped boundary, joined together in substantially the same way as described.

FIG. 6 shows the prosthetic valve 200 or 300 deployed in a native mitral annulus 11 of a patient, with the proximal end 230, 330 of the stent disposed in the left atrium 13 and the distal end 232, 332 of the stent disposed in the left ventricle 15. The prosthetic valve 200 or 300 may be installed in the native mitral annulus 11, such that the native valve leaflets are compressed against the native mitral annulus outside of the prosthetic valve. Using the prosthetic valve 200 or 300 in the native mitral annulus 11 may minimize interference between the distal end 232, 332 of the stent and the chordae tendineae in the left ventricle compared to conventional prosthetic valves, due to the relatively short aortic section of the valve 200, 300.

The distal end of the stent extending into the left ventricle may be designed not to flare radially outward relative to the proximal end 230, 330 of the stent. Such a design may further minimize interference between the distal end 232, 332 of the stent and the chordae tendineae. The proximal end 230, 330 of the stent extending into the left atrium may be designed to flare radially outward relative to the distal end 232, 332 of the stent. Such a design may enhance sealing of the valve 200 or 300 against the native mitral annulus 11. As described above with respect to FIGS. 4B and 5, the valve 200 or 300 may have proximal and distal cuffs made from different materials or having different thicknesses, so that improved sealing against the native mitral annulus 11 may be obtained with no impact or a minimal impact on the crimped diameter of the cuff.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve configured to be expanded between native leaflets of a native aortic annulus of a patient, the prosthetic heart valve comprising:

a stent having an expanded use condition and a collapsed condition, the stent in the expanded condition having a longitudinal axis, a proximal end, a distal end, an annulus section adjacent the proximal end, and an aortic section adjacent the distal end, the stent defining a flow direction from the proximal end toward the distal end, the annulus section including a plurality of collapsible cells each having a perimeter and an open center, and the aortic section including a plurality of fingers spaced from one another in an annular direction of the stent, the aortic section being devoid of structure between annularly adjacent ones of the fingers, whereby the annularly adjacent ones of the fingers are not directly connected to one another;

a cuff attached to the stent, the cuff having a distal edge and a proximal edge, the cuff being configured such that some of the plurality of cells distal to the distal edge are open cells at least partially devoid of the cuff, the cuff having a landing zone that is a continuous cylindrical portion of the cuff, a length of the landing zone being defined between the proximal edge of the cuff and a proximalmost location along the distal edge of the cuff when the stent is in the expanded use condition, the cuff including a proximal portion and a distal portion, the proximal portion consisting of a single layer and being coupled to, and entirely covering, a first group of the plurality of cells adjacent the proximal edge, the distal portion consisting of a single layer and being coupled to a second group of the plurality of cells adjacent the distal edge, the proximal portion being formed from a first material having a first average thickness in a radial direction perpendicular to the flow direction, and the distal portion being formed from a second material having a second average thickness in the radial direction perpendicular to the flow direction, the first average thickness being greater than the second average thickness; and a plurality of prosthetic valve leaflets attached to the cuff, each of the plurality of prosthetic valve leaflets having a free edge, wherein the entire free edge of each of the prosthetic valve leaflets is located within a first distance in the flow direction from the distal end of the stent when the prosthetic valve leaflets are in an open position and the stent is in the expanded use condition, the first distance being less than the length of the landing zone in the flow direction.

2. The prosthetic heart valve as claimed in claim 1, wherein the stent has a length between the proximal end and the distal end when the stent is in the expanded use condition, and the length of the landing zone is at least one-third of the length of the stent.

3. The prosthetic heart valve as claimed in claim 1, wherein each of the cells in the annulus section includes a plurality of apices, and each of the fingers extends from an apex of a respective one of the cells.

4. The prosthetic heart valve as claimed in claim 1, wherein the plurality of cells are arranged in a plurality of annular rows about the stent, and each of the fingers extends from the apex of a respective one of the cells in the annular row farthest from the proximal end of the stent.

5. The prosthetic heart valve as claimed in claim 1, wherein each of the fingers has a free end, the stent further including a retaining element connected to the free end of select ones of the fingers.

6. The prosthetic heart valve as claimed in claim 1, wherein the landing zone extends at least 16 mm in the flow direction between the proximal edge of the cuff and a proximal end of a most proximal cell of the open cells when the stent is in the expanded use condition.

7. The prosthetic heart valve as claimed in claim 1, wherein the stent has a length between the proximal end and the distal end when the stent is in the expanded use condition, and the free edge of each of the prosthetic valve leaflets is located at least three-fifths of the length of the stent above the proximal end of the stent when the prosthetic valve leaflets are in the open position and the stent is in the expanded use condition.

8. The prosthetic heart valve as claimed in claim 1, wherein the distal portion of the cuff includes a plurality of pockets containing a material that swells in size when contacted by blood.

9. The prosthetic heart valve as claimed in claim 8, wherein the plurality of pockets are formed from a porous membrane embedded with microspheres that swell in size when contacted by blood.

10. The prosthetic heart valve as claimed in claim 1, wherein the plurality of cells are arranged in a plurality of annular rows about the stent, the proximal portion of the cuff occupies every cell in a first row of the plurality of annular rows of cells and a first portion of every cell in a second row of the plurality of annular rows of cells adjacent the first row, and the distal portion of the cuff occupies a second portion of every cell in the second row of the plurality of annular rows of cells and a subset of cells in a third row of the plurality of annular rows of cells adjacent the second row, such that at least some of the open cells are located in the third row.

11. The prosthetic heart valve as claimed in claim 10, wherein the stent includes a plurality of commissure features spaced from one another in the annular direction of the stent, lateral edges of the leaflets being attached to the commissure features, and the cells in the third row occupied by the distal portion of the cuff are directly proximal of the commissure features.

12. The prosthetic heart valve as claimed in claim 1, wherein the proximal portion of the cuff is initially separate from the distal portion of the cuff and is joined to a proximal edge of the distal portion of the cuff at a distal edge of the proximal portion of the cuff.

13. The prosthetic heart valve as claimed in claim 12, wherein the proximal portion of the cuff is joined to the distal portion of the cuff along a boundary line that extends in a substantially circular closed curve about a circumference of the stent, the curve lying in a plane generally perpendicular to the flow direction.

14. The prosthetic heart valve as claimed in claim 1, wherein the proximal portion of the cuff and the distal portion of the cuff are made from different materials.

15. The prosthetic heart valve as claimed in claim 14, wherein the proximal portion of the cuff is made from a first material having a first average thickness in a radial direction perpendicular to the flow direction and the distal portion of the cuff is made from a second material having a second average thickness in the radial direction perpendicular to the flow direction, the first average thickness being greater than the second average thickness.

16. The prosthetic heart valve as claimed in claim 1, further comprising a connecting element interconnecting the plurality of fingers around the aortic section of the stent.

17. The prosthetic heart valve as claimed in claim 16, wherein the connecting element is formed of a porous material.

18. The prosthetic heart valve as claimed in claim 1, wherein the distal portion of the cuff is formed of a thinner material than the proximal portion of the cuff.

19. A prosthetic heart valve configured to be expanded between native leaflets of a native aortic annulus of a patient, the prosthetic heart valve comprising:

a stent having an expanded use condition and a collapsed condition, the stent in the expanded condition having a longitudinal axis, a proximal end, a distal end, an annulus section adjacent the proximal end, and an aortic section adjacent the distal end, the stent defining a flow direction from the proximal end toward the distal end, the annulus section including a plurality of collapsible cells each having a perimeter and an open center;

a cuff attached to the stent, the cuff having a distal edge and a proximal edge, the cuff being configured such that some of the plurality of cells distal to the distal edge are open cells at least partially devoid of the cuff, the cuff having a landing zone that is a continuous cylindrical portion of the cuff, a length of the landing zone being defined between the proximal edge of the cuff and a proximalmost location along the distal edge of the cuff when the stent is in the expanded use condition, the cuff including a proximal portion and a distal portion, the proximal portion being coupled to, and entirely covering, a first group of the plurality of cells adjacent the proximal edge, the distal portion being coupled to a second group of the plurality of cells adjacent the distal edge, the proximal portion being formed from a first layer having a first average thickness in a radial direction perpendicular to the flow direction, and the distal portion being formed from a second layer having a second average thickness in the radial direction perpendicular to the flow direction, the first average thickness being greater than the second average thickness; and a plurality of prosthetic valve leaflets attached to the cuff, each of the plurality of prosthetic valve leaflets having a free edge;

wherein the distal portion and the proximal portion each consist of a single layer of material.

* * * * *